(12) United States Patent
Baumfalk et al.

(10) Patent No.: US 12,314,881 B2
(45) Date of Patent: May 27, 2025

(54) METHOD FOR SUPPORTING A USER OF A BIOTECHNOLOGICAL LABORATORY

(71) Applicant: Sartorius Lab Instruments GmbH & Co. KG, Goettingen (DE)

(72) Inventors: Reinhard Baumfalk, Goettingen (DE); Kai Gloth, Goettingen (DE); Pasi Kankaanpaeae, Goettingen (DE); Rico Luedeke, Hardegsen (DE); Thomas Schink, Goettingen (DE)

(73) Assignee: Sartorius Lab Instruments GmbH & Co. KG, Goettingen (DE)

( * ) Notice: Subject to any disclaimer, the term of this patent is extended or adjusted under 35 U.S.C. 154(b) by 124 days.

(21) Appl. No.: 17/383,914

(22) Filed: Jul. 23, 2021

(65) Prior Publication Data
US 2022/0101218 A1  Mar. 31, 2022

(30) Foreign Application Priority Data

Sep. 28, 2020 (EP) ..................................... 20198782

(51) Int. Cl.
*G06Q 10/06* (2023.01)
*G06Q 10/0631* (2023.01)
(Continued)

(52) U.S. Cl.
CPC ... *G06Q 10/0633* (2013.01); *G06Q 10/06312* (2013.01); *G06Q 10/06316* (2013.01); *G06Q 10/0639* (2013.01)

(58) Field of Classification Search
CPC .................................................... G06Q 10/06
See application file for complete search history.

(56) References Cited

U.S. PATENT DOCUMENTS

| | | | |
|---|---|---|---|
| 2007/0092869 A1* | 4/2007 | Fulmer-Smentek | ... G16B 25/30 435/5 |
| 2007/0208800 A1* | 9/2007 | Frohlich | ................ G06Q 10/10 726/3 |

(Continued)

FOREIGN PATENT DOCUMENTS

| | | | | |
|---|---|---|---|---|
| JP | 2019032300 | | 2/2019 | |
| WO | WO-2007064357 A1 * | | 6/2007 | ........... G06F 16/489 |

(Continued)

OTHER PUBLICATIONS

M. Sargent (Ed.), Guide to achieving reliable quantitative LC-MS measurements, RSC Analytical Methods Committee, 2013. (Year: 2013).*

(Continued)

*Primary Examiner* — Kurtis Gills
(74) *Attorney, Agent, or Firm* — Pauly, DeVries Smith & Deffner LLC

(57) ABSTRACT

A method for supporting a user of a biotechnological laboratory to execute a biotechnological experiment with a real life experiment workflow in the laboratory based on a nominal experiment workflow using a data processing system comprising data processing modules, wherein in an offline planning routine, the nominal experiment workflow is defined by an offline planning module based on user input, wherein in a noncompliance routine, based on the monitoring information, noncompliance of the real life experiment workflow with the nominal experiment workflow is detected based on noncompliance criteria by a noncompliance module and in case of detection of noncompliance, a reaction routine is activated by the noncompliance module. In the offline planning routine, for each of the nominal workflow items an allowed variability regarding the number, the type, (Continued)

the resource and the parameter set of the at least one nominal workflow step may be individually defined.

19 Claims, 3 Drawing Sheets

(51) Int. Cl.
*G06Q 10/0633* (2023.01)
*G06Q 10/0639* (2023.01)

(56) References Cited

U.S. PATENT DOCUMENTS

| | | | | |
|---|---|---|---|---|
| 2009/0132285 | A1* | 5/2009 | Jakobovits | G06F 3/0482 |
| | | | | 726/17 |
| 2009/0316977 | A1 | 12/2009 | Juncker et al. | |
| 2010/0315083 | A1* | 12/2010 | Pauli | G01R 33/46 |
| | | | | 324/309 |
| 2013/0290963 | A1* | 10/2013 | Simske | G06Q 50/18 |
| | | | | 718/100 |
| 2016/0188769 | A1* | 6/2016 | Aylott | G06Q 50/06 |
| | | | | 703/6 |
| 2017/0067926 | A1 | 3/2017 | Meyberg | |
| 2018/0165604 | A1* | 6/2018 | Minkin | G06Q 10/06 |
| 2019/0120866 | A1 | 4/2019 | Knafel et al. | |
| 2021/0063410 | A1* | 3/2021 | Wilcox | G01N 33/6842 |

FOREIGN PATENT DOCUMENTS

| | | |
|---|---|---|
| WO | 2019050966 | 3/2019 |
| WO | 2020016123 | 1/2020 |

OTHER PUBLICATIONS

M. Sargent (Ed.), Guide to achieving reliable quantitative LC-MS measurements, RSC Analytical Methods Committee, 2013. (Year: 2013) (Year: 2013).*

"European Search Report," for European Patent Application No. 20198782 mailed Feb. 18, 2021 (9 pages).

* cited by examiner

METHOD FOR SUPPORTING A USER OF A BIOTECHNOLOGICAL LABORATORY

CLAIM OF PRIORITY

This application claims the benefit of European Patent application No. EP 20 198 782.3 filed on Sep. 28, 2020, the disclosure of which is incorporated herein by reference.

FIELD OF THE TECHNOLOGY

The present disclosure relates to a method for supporting a user of a biotechnological laboratory to execute a biotechnological experiment, a data processing system for realizing such a method, a computer program product and a computer readable storage media.

BACKGROUND

A biotechnological laboratory is generally understood to be a laboratory, in which biotechnological processes, in particular biopharmaceutical processes, can be carried out or supported. Those biotechnological processes are to be counted to the field of bioprocesses in general, however, include the technical means and methods to conduct the respective process. The term "bioprocess" presently represents processes that use either complete living cells or their components (e.g. mammalian cells, tissues, microorganisms, enzymes, chloroplasts, etc.) in order to manufacture products.

An example for an above noted biotechnological process is the use of a bioreactor to cultivate microorganisms or mammalian cells under given conditions, wherein a fermentation broth is transferred from the bioreactor to a downstream process.

Biotechnological production follows fixed process rules, allowing only very little tolerances. The situation for biotechnological experiments is quite the opposite. Variations are present at most of the time, which is actually the basis for new and unexpected solutions. This is why computer based support systems, that rely on the execution of more or less fixed workflows, have not been widely introduced into the world of biotechnological experiments.

A known approach for such a computer based support system (WO 2020/016123 A1) goes back to the definition of a nominal experiment workflow consisting of nominal workflow steps and navigating the user through this nominal experiment workflow with a corresponding information output to the user.

Any time, the user deviates from the nominal experiment workflow, the support system dispatches a warning and gives the user the opportunity to adapt the nominal experiment workflow to the real life experiment workflow. As the success of a biotechnological experiment basically depends on those variations, in order to be able to discover new and unexpected solutions, the known computer based support system is not a promising approach.

SUMMARY

It is therefore an object of the present disclosure to provide a method for supporting a user of a biotechnological laboratory that meets the requirements of a biotechnological experiment.

The above noted problem is solved for a method with the features as described herein.

Before the idea underlying the disclosure is presented, a brief explanation of the general structure of the proposed method is given.

The proposed method serves for supporting the user of a biotechnological laboratory to execute a biotechnological experiment with a real life experiment workflow in this laboratory. The real life experiment workflow is based on a nominal experiment workflow that has been defined as a preparation of the real life experiment and accordingly, before the real life experiment workflow has been started. The proposed method is designed as a computer supported method using a data processing system comprising certain data processing modules.

Presently, the expression "real life" means, that the corresponding action item is actually taking place in the laboratory. The expression "nominal" means, that the corresponding action item is planned, which action item is to be realized in real life at the appropriate time based on the respective planning information.

Presently, each experiment workflow, be it real life or nominal, consists of at least one workflow item. Each workflow item consists of at least one workflow step. Each workflow step is specified by a type and/or a resource and/or a parameter set. The type describes the kind of action that is represented by the workflow step. The resource describes the device, media or any other component needed to perform the workflow step. The parameter set describes the values to be set for performing the workflow step.

Before the real life experiment workflow is started, in an offline planning routine, the nominal experiment workflow is defined in a nominal workflow data structure. This is done by an offline planning module of the data processing system, in some embodiments, but not necessarily, based on user input. For this user input, a user interface may be provided, that allows to define the experiment workflow. As an alternative or in addition, it may be possible that in the offline planning routine, the nominal experiment workflow is downloaded from another device, a cloud service, or the like. It may also be possible, that the nominal experiment workflow is derived from a previous real life workflow, that has been performed and recorded beforehand. This recording may well be done by the proposed data processing system, which then can provide a corresponding recording routine.

After the real life experiment workflow has been started, in a monitoring routine, monitoring information relating to the real life workflow steps is retrieved from the laboratory and stored during the experiment. This is done by a monitoring module of the data processing system.

In an execution routine, control information is provided to the user and/or the laboratory regarding the execution of a nominal workflow step. This is done by an execution module of the data processing system.

Finally, in a noncompliance routine, based on the monitoring information, noncompliance of the real life experiment workflow with the nominal experiment workflow is detected based on noncompliance criteria by a noncompliance module. In case of such detection of noncompliance, a reaction routine is actuated in the noncompliance module, which reaction routine may dispatch a warning to the user via a user interface.

Based on this structure, the idea underlying the disclosure is to take into account all above noted variations that are immanent to the biotechnological experiment already in the offline planning routine. This means that the proposed method works with those variations starting from the offline planning routine and ending with the last real life workflow step of the real life experiment workflow. According to the proposed solution, variations are not allowed only regarding parameters, but basically to any aspect which is relevant to the experiment.

With the proposed solution a particularly effective process in biotechnological experiments is possible, as the occurrence of variations does not lead to an interruption of the process itself. In addition it has been found out, that the allowed variations give room for optimization for example in the field of resource planning, which will be explained later.

In detail, it is proposed, that in the offline planning routine, for at least one of the nominal workflow items, in some embodiments for each of the nominal workflow items, an allowed variability regarding at least one of the number, the type, the resource and the parameter set of the at least one nominal workflow step is individually defined. In some embodiments, it is proposed, that in the offline planning routine, for each of the nominal workflow items an allowed variability regarding the number, the type, the resource and the parameter set of the at least one nominal workflow step is individually defined.

On the one hand this means, that the number of nominal workflow steps assigned to a nominal workflow item may generally be subject to such variability. On the other hand, this means, that, each and any nominal workflow step of a nominal workflow item can be individually assigned a specific variability. It may be pointed out, that the allowed variability may regard additional aspects of the respective workflow item, such that the above noted list is not necessarily complete.

The term "individually" with respect to the definition of the allowed variability means, that in the offline planning routine, each respective workflow item and with it each of its workflow steps may be assigned a specific variability as indicated above.

In the noncompliance routine, the criteria for noncompliance are fulfilled by, according to the monitoring information, a real life workflow item having moved beyond the allowed variability of the corresponding nominal workflow item of the nominal experiment workflow. This means that in case any one of the nominal workflow items of the nominal experiment workflow move beyond the allowed, individually defined variability, the criteria for noncompliance are fulfilled, such that an above noted reaction routine is activated. As long as the real life experiment workflow stays within the individually defined variability, the real life experiment workflow may proceed as has been planned in the offline planning routine.

Various embodiments specify variants for the definition of the allowed variability. Some embodiments are directed to the number of the at least one workflow step, which is assigned to the respective workflow item, being subject to the allowed variability, which allows to define a high flexibility for the user, who is conducting the experiment. Some embodiments are directed to the type and/or the resource of the respective workflow step being subject to the allowed variability, which allows to define the allowed variability within specific borders. An embodiment clarifies, that the definition of the allowed variabilities is conducted for at least two workflow items individually in the above noted sense.

Various embodiments are directed to a detailed definition of the respective variabilities. Here it becomes especially apparent that the proposed solution does not only take into account a variability regarding a parameter deviation, but also variabilities in all relevant aspects, even in the aspect of the number of workflow steps in a workflow item.

Various embodiments are directed to possibilities to cope with the defined variabilities during the experiment and even to use those variabilities to optimize the resource planning.

Various embodiments are directed to an important aspect in any experiment, which is the definition of reference points within the nominal experiment workflow. Such reference points serve to define reference criteria, which allow the assessment, whether the experiment is successful or not. Such reference criteria may be a measurement value, which has to be exceeded for the experiment to be qualified as "successful".

Even here, the definition of the variabilities in the offline planning routine is advantageous. This is because, according to an embodiment, in case of the reference criteria not having been met, information regarding the allowed variability of the nominal workflow steps of the experiment is provided to the user. This allows the user to evaluate, which variability has led to the unsuccessful result of the experiment.

A realistic definition of the allowed variability of the respective parameter set is of utmost importance for the user of the biotechnological laboratory. In many cases, this variability goes back to experiences within previous experiments. Accordingly, in some embodiments, a learning routine is proposed, which allows to derive the variability from the monitoring information gained in previous real life workflows. An easy way to realize this is to define the variability based on the extreme values for the respective parameter, that have been gained in the previous experiments. With this it is possible for the respective variabilities to automatically transform into values that lead the user of a biotechnological laboratory to optimal results.

Additional embodiments are directed to the data processing system including the above noted modules as such.

The proposed data processing system is configured to conduct the proposed method, such that all explanations given for the proposed method are fully applicable to the proposed data processing system.

According to further embodiments, a computer program product for a proposed data processing system is provided. The computer program product is configured to realize the above noted, proposed method, which particularly includes the realization of the above noted routines. Again, all explanations given for the proposed method are fully applicable to the proposed computer program product.

According to further embodiments, a computer readable storage media, on which the computer program is stored, is provided. Again all explanations given for the proposed method are fully applicable to the proposed readable storage media.

Various embodiments provide a method for supporting a user of a biotechnological laboratory to execute a biotechnological experiment with a real life experiment workflow in the laboratory based on a nominal experiment workflow using a data processing system comprising data processing modules, wherein each experiment workflow consists of at least one workflow item, each consisting of at least one workflow step, wherein each workflow step is specified by a type and/or by a required resource and/or by a parameter set consisting of at least one parameter describing the values to be set, wherein in an offline planning routine, the nominal experiment workflow is defined by an offline planning module, such as based on user input, wherein in a monitoring routine, monitoring information relating to the real life workflow steps is retrieved from the laboratory and stored during the experiment by a monitoring module, wherein in an execution routine, control information is provided to the user and/or the laboratory regarding the execution of nominal workflow steps by an execution module, wherein in a noncompliance routine, based on the monitoring information, noncompliance of the real life experiment workflow with the nominal experiment workflow is detected based on noncompliance criteria by a noncompliance module and in case of detection of noncompliance, a reaction routine is activated by the noncompliance module, wherein in the offline planning routine, for at least one of the nominal workflow items an allowed variability regarding at least one of the number, the type, the resource and the parameter set of the at least one nominal workflow step is individually defined and that in the noncompliance routine, the criteria for noncompliance are fulfilled by, according to the monitoring information, a real life workflow item having moved beyond the allowed variability of the corresponding nominal workflow item of the nominal experiment workflow.

In various embodiments, in the offline planning routine, for at least one of the nominal workflow items an allowed variability regarding the number of the at least one nominal workflow step is individually defined.

In various embodiments, in the offline planning routine, for at least one of the nominal workflow items an allowed variability regarding the type and/or the resource of the at least one nominal workflow step is individually defined.

In various embodiments, in the offline planning routine, for at least two of the nominal workflow items, such as for each of the nominal workflow items, an allowed variability regarding at least one of the number, the type, the resource and the parameter set of the at least one nominal workflow step is individually defined.

In various embodiments, the allowed variability regarding the number of the at least one nominal workflow step is defined as a minimum number of workflow steps and/or as a maximum number of workflow steps, and/or, that the allowed variability regarding the type of the at least one nominal workflow step is defined as a group of applicable types, and/or, that the allowed variability regarding the resource of the at least one nominal workflow step is defined as a group of applicable resources, and/or, that the allowed variability regarding the parameter set is defined as a range in the respective parameter.

In various embodiments, in an inline planning routine, the oncoming nominal workflow steps, that are not yet executed, are adjusted to the executed real life workflow steps by an inline planning module, such as, that with each execution of a real life workflow step, in the inline planning routine, the oncoming nominal workflow steps are adjusted.

In various embodiments, the adjustment of the oncoming nominal workflow steps is performed based on a consistency rule set, which represents predefined dependencies between sequential workflow steps to ensure biotechnological consistency between those workflow steps.

In various embodiments, in the inline planning routine, for each oncoming workflow step the on site resources in the laboratory required for its respective execution are defined based on the respective nominal workflow step.

In various embodiments, the definition of the on site resources for each oncoming workflow step is performed based on at least one optimization criterion, taking into account the variability of the nominal workflow items, such as, that the optimization criteria are directed to the minimization of costs and/or time consumption.

In various embodiments, by a resource management module, availability information regarding on site resources in the laboratory is provided and that in the inline planning routine, based on the availability information, on site resources are defined for the oncoming workflow steps.

In various embodiments, in the inline planning routine, in case of non availability of a resource, based on a replacement rule set, the resource is replaced by an available resource and defined for the respective nominal workflow step.

In various embodiments, in the offline planning routine, at least one reference point within the nominal experiment workflow may be defined based on user input, which reference point is assigned reference criteria, such as, that in case of the reference criteria are not being met, information regarding the allowed variability of the nominal workflow steps of the experiment is provided to the user.

In various embodiments, in a learning routine, from the stored monitoring information of previously executed real life workflows, for at least part of the nominal workflow items, an allowed variability regarding the parameter set of the at least one nominal workflow step is individually defined.

In various embodiments, in the learning routine, from the stored monitoring information of at least two previously executed real life workflows, the extreme values for at least one parameter of the parameter set are evaluated and that the variability for this parameter is defined based on those extreme values.

Various embodiments provide a data processing system for realizing a method for supporting a user of a biotechnological laboratory to execute a biotechnological experiment with a real life experiment workflow in the laboratory based on a nominal experiment workflow, a method as described herein, wherein the data processing system comprises data processing modules, wherein each experiment workflow consists of at least one workflow item, each consisting of at least one workflow step, wherein each workflow step is specified by a type and/or by a required resource and/or by a parameter set consisting of at least one parameter describing the values to be set, wherein the data processing system comprises an offline planning module, by which in an offline planning routine, the nominal experiment workflow is defined, such as based on user input, wherein the data processing system comprises a monitoring module, by which in a monitoring routine, monitoring information relating to the real life workflow steps is retrieved from the laboratory and stored during the experiment, wherein the data processing system comprises an execution module, by which in an execution routine, control information is provided to the user and/or the laboratory regarding the execution of nominal workflow steps, wherein the data processing system comprises a noncompliance module, by which in a noncompliance routine, based on the monitoring information, noncompliance of the real life experiment workflow with the nominal experiment workflow is detected based on noncompliance criteria and in case of detection of noncompliance, a reaction routine is activated by the noncompliance module, wherein the offline planning module configured such that in the offline planning routine, for at least one of the nominal workflow items an allowed variability regarding at least one of the number, the type, the resource and the parameter set of the at least one nominal workflow step may be individually defined and that the noncompliance module is configured such that in the noncompliance routine, the criteria for noncompliance are fulfilled by, according to the monitoring information, a real life workflow item having moved beyond the allowed variability of the corresponding nominal workflow item of the nominal experiment workflow.

Various embodiments provide a computer program product for a data processing system as described herein.

Various embodiments provide a computer readable storage media, on which a computer program product as described herein, such as in a non volatile manner.

BRIEF DESCRIPTION OF THE DRAWINGS

In the following, an embodiment of the disclosure is explained with respect to the drawings. In the drawings show FIG. 1 according to a proposed method a) the nominal experiment workflow and b) the real life experiment workflow at the point in time to, each regarding a biotechnological experiment and FIG. 2 the basic structure of a data processing system designed to realize the proposed method shown in FIG. 1, FIG. 3 an overview of the result of the monitoring route for a number of experiment cycles.

DETAILED DESCRIPTION

Figure 1:
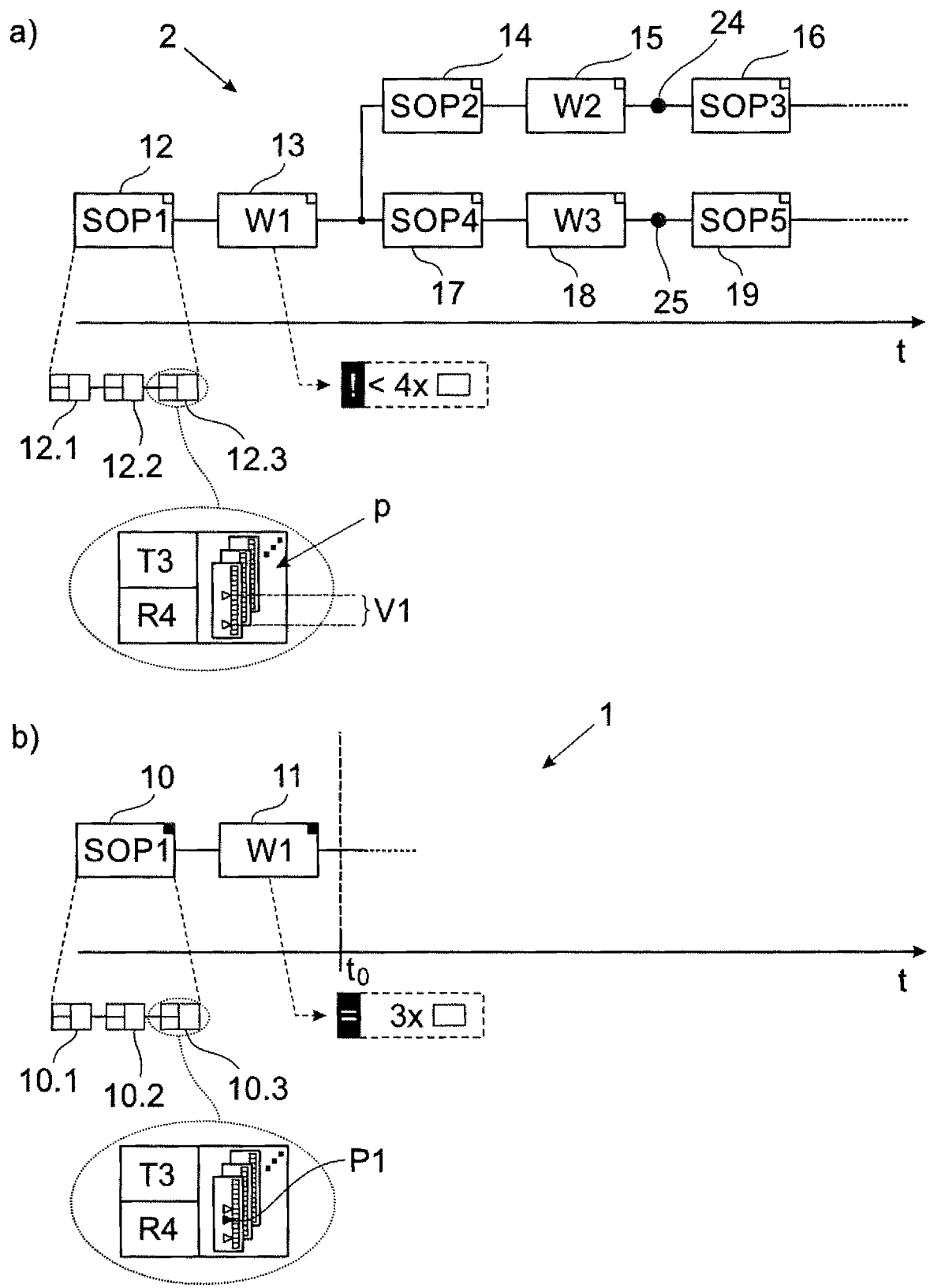

The proposed method serves to support a user of a biotechnological laboratory to execute a biotechnological experiment with a real life experiment workflow 1 in the laboratory based on a nominal experiment workflow 2 using a data processing system 3 comprising data processing modules 4-9.

The data processing system 3 may be a single computer with the usual components processor and storage. However, the data processing system 3 may well be realized as a decentralized computer system with numerous distributed computer components, that may even at least partly be provided by a cloud-structure.

Each experiment workflow, be it real life or nominal, consists of at least one workflow item 10-19, each consisting of at least one workflow step 10.1-10.3, 12.1-12.3. Each workflow step may be specified by a type such as "pouring step", "withdrawing step", "mixing step", "filtering step", and/or by a required resource such as "pipette", "mixer", "filter", "media a", "media b" and/or by a parameter set consisting of at least one parameter describing the values to be set such as "volume", "mixing speed", "filter parameters" etc.

In an offline planning routine, which is performed before starting the real life experiment workflow 1, the nominal experiment workflow 2 is defined in a nominal workflow data structure 20 by an offline planning module 4, such as based on user input. Such user input may be conducted via a user interface 21 indicated in FIG. 2. In a monitoring routine, monitoring information relating to the real life workflow steps 10.1-10.3 is retrieved from the laboratory and stored during the experiment by a monitoring module 5. In an execution routine, control information is provided to the user and/or the laboratory regarding the execution of nominal workflow steps 10.1-10.3 by an execution module 6.

In a noncompliance routine, based on the monitoring information, noncompliance of the real life experiment workflow 1 with the nominal experiment workflow 2 is detected based on noncompliance criteria by a noncompliance module 7. In case of detection of noncompliance, a reaction routine is activated in the noncompliance module 7. Such reaction routine may be the dispatch of a warning message to the user via the user interface 21. It may also be provided, that in case of the detection of noncompliance, the real life experiment workflow 1 is terminated.

Figure 2:
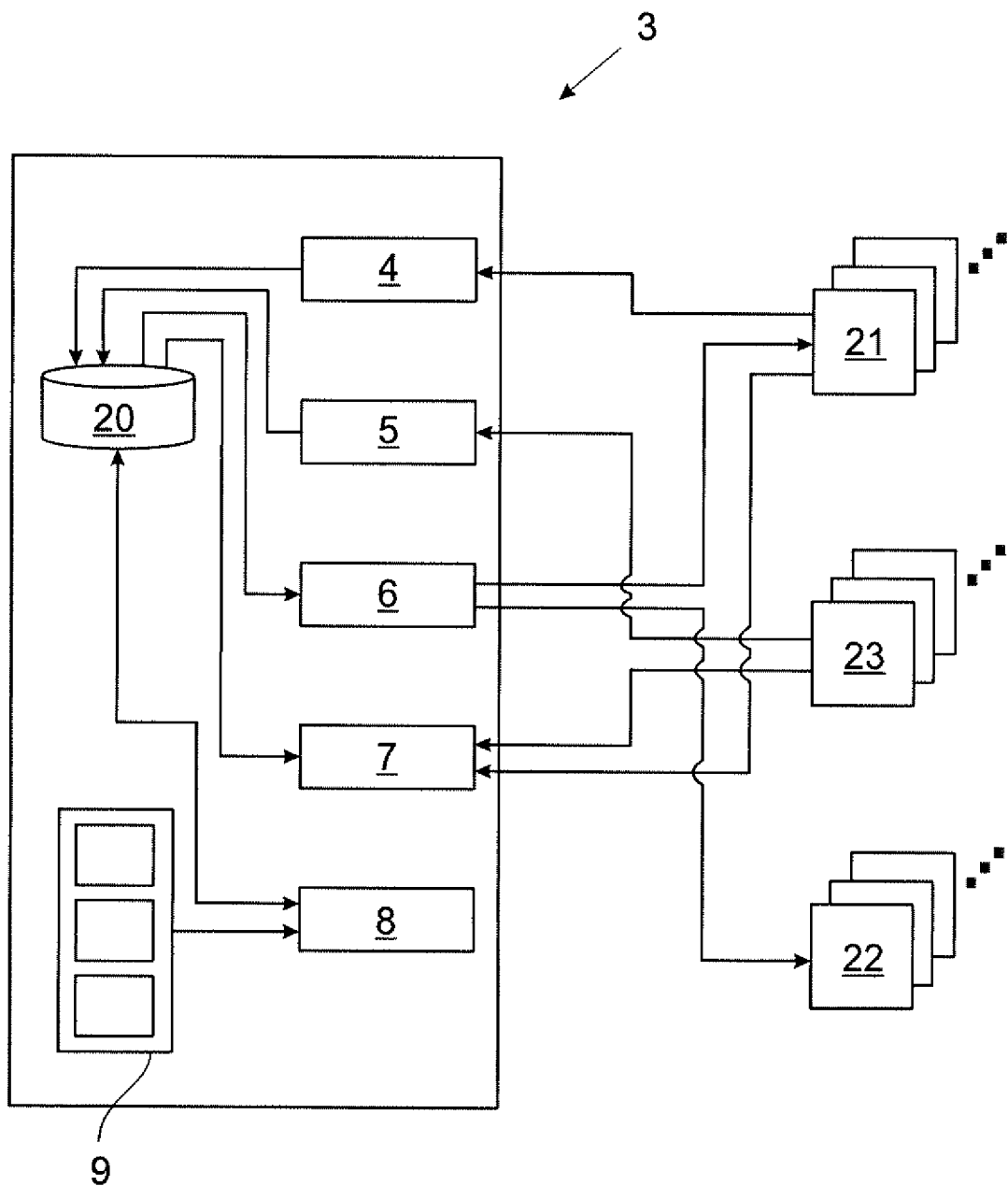

The user interface 21 may be any kind of user interface, which may be part of the proposed data processing system 3, or, as shown in FIG. 2, may be realized separately from the proposed data processing system 3. Depending on the overall structure of the data processing system 3, the user interface 21 may well be a smart device, such as a smart phone, a tablet or the like. As also indicated in FIG. 2, the user interface 21 may include a number of different interface units.

The above noted execution routine may be realized in different ways. In a first alternative, the control information is provided to the user via the user interface 21. In this case, the user can be provided with information regarding the oncoming nominal workflow steps.

As an alternative or in addition, the control information may be provided to the laboratory, which means to the devices within the laboratory. In FIG. 2, those devices are indicated with reference number 22. In this case, the control information triggers actions of the devices such as the start of a mixing process or the switching of a valve.

Even the monitoring information may be retrieved from the user interface 21 by the user typing in the respective information via the user interface 21. In some embodiments, however, the monitoring information is retrieved from sensors 23 within the laboratory. Those sensors 23 may be part of the devices 22. As an alternative or in addition, at least part of those sensors 23 are realized as stand-alone components.

In some embodiments, in the offline planning routine, for at least one of the nominal workflow items 12-19, such as for each of the nominal workflow items 12-19, an allowed variability regarding the number and at least one of the type, the resource and the parameter set of the at least one nominal workflow step 12.1-12.3 is individually defined. The variability may, for example, be represented by a number of variables, which contain the information of the variability in the different, above noted regards.

In the noncompliance routine, the criteria for noncompliance are fulfilled by, according to the monitoring information, a real life workflow item 10,11 having moved beyond the allowed variability of the corresponding nominal workflow item 12, 13 of the nominal experiment workflow 2.

The proposed solution is represented by FIG. 1. The nominal experiment workflow 2 is shown in FIG. 1a), which shows nominal workflow items 12-19, each of which comprise nominal workflow steps 12.1-12.3. Those workflow steps 12.1.-12.3 are shown only for nominal workflow item 12 as an example. From the detailed view in FIG. 1a) it becomes apparent that the nominal workflow step 12.3 is described by the type T3, the resource R4 and a parameter set p. The type T3 may be a specified "pouring step" or the like, while the resource R4 may be any kind of pouring device or the like. Interesting regarding this nominal workflow item 12.3 is the fact, that at least one parameter $p_i$ of the parameter set p is assigned a variability in the form of a range in the respective parameter. This variability in the form of a range is indicated with reference V1 in FIG. 1a).

In FIG. 1a) the workflow items 12-19 are labeled with "SOPX" or with "WX". This means, that the workflow items 12,14,16,17,19 are to be considered "standard operating procedures", which are normally defined in a rigid manner. This corresponds to the detailed view in FIG. 1, which only allows a certain variability regarding the parameter set p. The workflow items 13,15,18, on the other hand, are hardly defined at all. As an example, workflow item 13 is assigned an allowed variability in the form a restricted number of workflow steps to the number of four. Other than that, the workflow item 13 is not defined. Those nominal workflow items 13,15,18 may be considered wildcard-items, as they are hardly restricted in any way. This means, that those nominal workflow items 13,15,18 allow the full freedom to experiment.

Only in order to clarify, what is possible with the proposed method, FIG. 1*a*) shows two extreme possibilities for the variability of nominal workflow items 12-19. It may be pointed out that the allowed variability may be adjusted anywhere in between those extremes, which makes the proposed method considerably powerful.

FIG. 1*b*) now shows the real life experiment workflow 1 at the point in time to, which corresponds to the nominal experiment workflow 2 shown in FIG. 1*a*). Accordingly, FIG. 1*b*) is a snap shot at the point in time to, in which the real life workflow items 10,11 have already been executed. The detailed view in FIG. 1*b*) shows, that the parameter with the variability V1 has been set to the value P1 in real life, which appears to be within the allowed variability. As also the type and the resource comply with the definition of the corresponding nominal workflow step 12.3, the noncompliance routine does not activate the reaction routine. The same is to be said for the real life workflow item 11, which, according to FIG. 1*b*), comprises only three real life workflow steps, which again is within the allowed variability.

It may be summed up that the user is free to move within the allowed variabilities without being disrupted by the proposed method, which makes the proposed method particularly user friendly.

In some embodiments, in the offline planning routine, for at least one of the nominal workflow items 12-19 an allowed variability regarding the number of the at least one nominal workflow step 12.1-12.3 is individually defined, as indicated above.

As an alternative or in addition, in the offline planning routine, for at least one of the nominal workflow items 12-19 an allowed variability regarding the type and/or the resource of the at least one nominal workflow step 12.1-12.3 is individually defined. This has been indicated above as well.

It is also possible, that in the offline planning routine, for at least two of the nominal workflow items 12-19, In some embodiments, for each of the nominal workflow items 12-19, an allowed variability regarding at least one of the number, the type, the resource and the parameter set of the at least one nominal workflow step 12.1-12.3 is individually defined. In some embodiments in the offline planning routine, for three, four or more of the nominal workflow items 12-19, such as for each of the nominal workflow items 12-19, an allowed variability regarding at least one of the number, the type, the resource and the parameter set of the at least one nominal workflow step 12.1-12.3 is individually defined.

Generally, the variability may be defined in a number of ways. The allowed variability regarding the number of the at least one nominal workflow step for example, may be defined as a minimum number of workflow steps and/or as maximum number of workflow steps. As an alternative or in addition, the allowed variability regarding the type of the at least one nominal workflow step may be defined as a group of applicable types. Again as an alternative or in addition the allowed variability regarding the resource of the at least one nominal workflow step may be defined as a group of applicable resources. Finally, as an alternative or in addition, the allowed variability regarding the parameter set may be defined as a range in the respective parameter, as indicated above.

Depending on the kind of the experiment, the oncoming nominal workflow items 14-19, that are not yet executed, may depend on the already executed real life workflow items, here the real life workflow items 10,11. This may for example be the case, if the wildcard-item 11 includes a pouring step with a specific fluid, that allows only specific subsequent workflow items in order to prevent biotechnological inconsistency and thereby failure of the biotechnological process.

Here, as an example, the real life workflow item 11 allows as subsequent workflow items only the upper range of nominal workflow items 14-16, and not the lower range of nominal workflow items 17-19. If this is a deterministic characteristic, it is possible, that in an inline planning routine, the oncoming nominal workflow items 14-19, that are not yet executed, are adjusted to the past real life workflow by an inline planning module 8 shown in FIG. 2. In some embodiments, this adjustment is even done with each execution of a real life workflow step.

The above noted adjustment of the oncoming nominal workflow items 14-19 can be performed based on a consistency rule set, which represents predefined dependencies between sequential workflow steps to ensure biotechnological consistency between those workflow steps.

In some embodiments, in the inline planning routine, for each oncoming workflow step, the on site resources required for its respective execution are defined based on the nominal workflow step. The expression "on site resources" relates to those resources that are actually available in the specific laboratory. Those resources include not only the devices, but also the media available in the specific laboratory as noted above. Other resources can be applied here as well.

The above noted definition of on site resources for each oncoming workflow step can be subject to an optimization. In detail, the definition of the on site resources for each oncoming workflow step is performed based on at least one optimization criterion, taking into account the variability of the nominal workflow items. In various embodiments, the optimization criteria are directed to the minimization of costs and/or time consumption.

Further, a resource management module 9 can be provided, by which availability information regarding on site resources in the laboratory is provided. In the inline planning routine 8, based on this availability information, on site resources are assigned to the workflow steps as noted above.

In the inline planning routine, in case of non-availability of a resource, based on a replacement rule set, the resource is replaced by an available resource.

In order to be able to assess, whether the experiment is successful or not, in the offline planning routine, at least one reference point 24,25, may be defined within the nominal experiment workflow 2 based on user input. The reference point 24,25 may be assigned reference criteria, which may be related to certain measurement values. In case of the reference criteria not being fulfilled, information regarding the allowed variability of the nominal workflow steps may be provided to the user via the user interface 21, for example. In the nominal experiment workflow 2 shown in FIG. 1*a*), this would mean to display variabilities, for example the parameter range V1 of nominal workflow item 12 or the variability in the number of nominal workflow items of nominal workflow item 13 noted above. With this information, the user may estimate, which variability has actually led to the unsuccessful outcome of the experiment.

Figure 3:
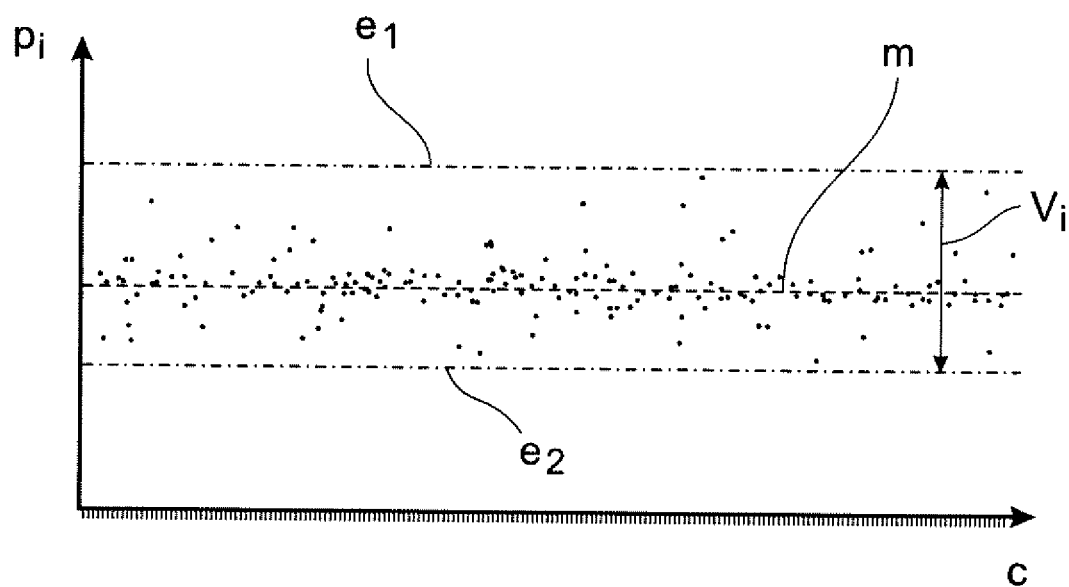

It has been noted already, that the result of the experiment often depends on the optimal definition of the variabilities of the respective parameter set. Therefore, according to some embodiments, a learning routine is proposed. In the learning routine, from the stored monitoring information of previously executed real life workflows 1, for at least part of the nominal workflow items 12-19, an allowed variability regarding the parameter set of the at least one nominal workflow step 12.1-12.3 is individually defined. This is shown in an example in FIG. 3. Here, for one nominal workflow step, one parameter $p_i$ of the parameter set p is shown for a number of previous experiments, which are depicted with reference c in FIG. 3. It may be extracted from FIG. 3, that the values for the parameter $p_i$ are distributed around an average value m. The extreme values, that result from this distribution, are represented by lines with reference values $e_1$ and $e_2$. In some embodiments, the variability for this parameter is defined based on those extreme values, just by defining the variability $V_i$ as the value range between the two extreme values $e_1$ and $e_2$. The above noted definition of the above noted variabilities may still be influenced by the user via the user interface 21. In particular in the example shown in FIG. 3, the user would be able to move the upper limit or the lower limit of the variability $V_i$, such that the variability $V_i$ may be manually adjusted.

It may also be pointed out, that according to another teaching, the above noted data processing system 3 is provided as such, which serves for realizing the method for supporting a user of a biotechnological laboratory to execute a biotechnological experiment with a real life experiment workflow 1 in the laboratory based on a nominal experiment workflow 2.

The proposed data processing system 3 comprises data processing modules 4-9, wherein each experiment workflow 1,2 consists of at least one workflow item 10-19, each consisting of at least one workflow step 10.1-10.3,12.1-12.3, wherein each workflow step 10.1-10.3, 12.1-12.3 is specified by a type and/or by a required resource and/or by a parameter set consisting of at least one parameter describing the values to be set, wherein the data processing system 3 comprises an above noted offline planning module 4, by which in an offline planning routine, the nominal experiment workflow 2 is defined, such as based on user input, wherein the data processing system 3 comprises an above noted monitoring module 5, by which in a monitoring routine, monitoring information relating to the real life workflow steps 10.1,10.2 is retrieved from the laboratory and stored during the experiment, wherein the data processing system 3 comprises an above noted execution module 6, by which in an execution routine, control information is provided to the user and/or the laboratory regarding the execution of nominal workflow steps 12.1-12.3, wherein the data processing system 3 comprises an above noted noncompliance module 7, by which in a noncompliance routine, based on the monitoring information, noncompliance of the real life experiment workflow 1 with the nominal experiment workflow 2 is detected based on noncompliance criteria and in case of detection of noncompliance, a reaction routine is activated by the noncompliance module 7. It is essential for this teaching, that the offline planning module 4 is configured such that in the offline planning routine, for at least one of the nominal workflow items 12-19 an allowed variability regarding at least one of the number, the type, the resource and the parameter set of the at least one nominal workflow step 12.1-12.3 may be individually defined and that the noncompliance module 7 is configured such that in the noncompliance routine, the criteria for noncompliance are fulfilled by, according to the monitoring information, a real life workflow item 10,11 having moved beyond the allowed variability of the corresponding nominal workflow item 12,13 of the nominal experiment workflow 2.

This means, that the data processing system 3 is configured to allow the definition of the above noted, allowed variabilities using the offline planning routine and also to conduct the proposed method up to the execution of the compliance routine using the above noted compliance module. As also noted above, the data processing system 3 may be a single computer with the usual components processor and storage. However, the data processing system 3 may well be realized as a decentralized computer system with numerous distributed computer components, that may at least partly be provided by a cloud-structure.

Finally, independent teachings are directed to a computer program product for the data processing system and to a computer readable storage media, on which the computer program product is stored.

The invention claimed is:

1. A method for supporting a user of a biotechnological laboratory to execute a biotechnological experiment with a real life experiment workflow in the laboratory based on a nominal experiment workflow using a data processing system comprising data processing modules and a plurality of devices, sensors and resources, the method comprising:
   providing at least one device having at least one sensor, and
   providing at least one required resource for performing the method,
   wherein each experiment workflow comprises at least one workflow item, each comprising at least one workflow step, wherein each workflow step is specified by a type and/or by a required resource and/or by a parameter set comprising at least one parameter describing the values to be set,
   wherein in an offline planning routine, the nominal experiment workflow is defined by an offline planning module based on user input,
   wherein in a monitoring routine, monitoring information relating real life workflow steps is retrieved from the sensor and stored during the experiment by a monitoring module,
   wherein in an execution routine, control information is provided to the user regarding the execution of oncoming nominal workflow steps by an execution module, wherein in a noncompliance routine, based on the monitoring information, noncompliance of the real life experiment workflow with the nominal experiment workflow is detected based on noncompliance criteria by a noncompliance module and in case of detection of noncompliance, a reaction routine is activated by the noncompliance module,
   wherein in the reaction routine, a warning is presented to the user via the user interface,
   wherein in the offline planning routine, for at least one nominal workflow item, an allowed variability is set within which the user is free to move, and the allowed variability regards at least one of the nominal workflow items, regarding at least one of the number, the type, the resource and the parameter set of the at least one nominal workflow step
   wherein in the noncompliance routine, the criteria for noncompliance are fulfilled by, according to the monitoring information, a real life workflow item having moved beyond the allowed variability of the corresponding nominal workflow item of the nominal experiment workflow, and wherein when a user has moved beyond the allowed variability of the corresponding nominal workflow item of the nominal experiment workflow the experimental process is terminated.

2. The method according to claim 1, wherein in the offline planning routine, for at least one of the nominal workflow items an allowed variability regarding the number of the at least one nominal workflow step is individually defined.

3. The method according to claim 1, wherein in the offline planning routine, for at least one of the nominal workflow items an allowed variability regarding the type and/or the resource of the at least one nominal workflow step is individually defined.

4. The method according to claim 1, wherein in the offline planning routine, for at least two of the nominal workflow items an allowed variability regarding at least one of the number, the type, the resource and the parameter set of the at least one nominal workflow step is individually defined.

5. The method according to claim 4, wherein the allowed variability regarding the number of the at least one nominal workflow step is defined as a minimum number of workflow steps and/or as a maximum number of workflow steps, and/or, that the allowed variability regarding the type of the at least one nominal workflow step is defined as a group of applicable types, and/or, that the allowed variability regarding the resource of the at least one nominal workflow step is defined as a group of applicable resources, and/or, that the allowed variability regarding the parameter set is defined as a range in the respective parameter.

6. The method according to claim 1, wherein in an inline planning routine, the oncoming nominal workflow steps, that are not yet executed, are adjusted to the executed real life workflow steps by an inline planning module.

7. The method according to claim 6, wherein the adjustment of the oncoming nominal workflow steps is performed based on a consistency rule set, which represents predefined dependencies between sequential workflow steps to ensure biotechnological consistency between those workflow steps.

8. The method according to claim 6, wherein in the inline planning routine, for each oncoming workflow step the on site resources in the laboratory required for its respective execution are defined based on the respective nominal workflow step.

9. The method according to claim 8, wherein the definition of the on site resources for each oncoming workflow step is performed based on at least one optimization criterion, taking into account the variability of the nominal workflow items.

10. The method according to claim 8, wherein by a resource management module, availability information regarding on site resources in the laboratory is provided and that in the inline planning routine, based on the availability information, on site resources are defined for the oncoming workflow steps.

11. The method according to claim 10, wherein in the inline planning routine, in case of non availability of a resource, based on a replacement rule set, the resource is replaced by an available resource and defined for the respective nominal workflow step.

12. The method according to claim 1, wherein in the offline planning routine, at least one reference point within the nominal experiment workflow may be defined based on user input, which reference point is assigned reference criteria, such that in case of the reference criteria are not being met, information regarding the allowed variability of the nominal workflow steps of the experiment is provided to the user.

13. A data processing system for realizing a method for supporting a user of a biotechnological laboratory to execute a biotechnological experiment with a real life experiment workflow in the laboratory based on a nominal experiment workflow, the data processing system comprising:

at least one sensor; and a plurality of data processing modules, wherein each experiment workflow comprises at least one workflow item, each comprising at least one workflow step, wherein each workflow step is specified by a type and/or by a required resource and/or by a parameter set comprising at least one parameter describing the values to be set, wherein within at least one workflow step a user is free to move within an allowed variability, wherein the data processing system comprises an offline planning module, by which in an offline planning routine, the nominal experiment workflow is defined based on user input wherein the data processing system comprises a monitoring module, by which in a monitoring routine, monitoring information relating to the real life workflow steps is retrieved from the laboratory and stored during the experiment, the monitoring information received from one or more sensors, wherein the data processing system comprises an execution module, by which in an execution routine, control information is provided to the user and/or the laboratory regarding the execution of oncoming nominal workflow steps, wherein the data processing system comprises a noncompliance module, by which in a noncompliance routine, based on the monitoring information, noncompliance of the real life experiment workflow by the user outside of the allowed variability with the nominal experiment workflow is detected based on noncompliance criteria and in case of detection of noncompliance, a reaction routine is activated by the noncompliance module, wherein in the reaction routine, a warning is presented to the user via the user interface, wherein the offline planning module configured such that in the offline planning routine, for at least one nominal workflow item an allowed variability, within which the at least one of the nominal workflow items is free to move, regarding at least one of the number, the type, the resource and the parameter set of the at least one nominal workflow step may be manually defined and that the noncompliance module is configured such that in the noncompliance routine, the criteria for noncompliance are fulfilled by, according to the monitoring information, a real life workflow item having moved beyond the allowed variability of the corresponding nominal workflow item of the nominal experiment workflow, and wherein when the real life workflow item has moved beyond the allowed variability the biological experiment terminates.

14. A computer program product for a data processing system, wherein the data processing system comprises:

at least one sensor; and a plurality of data processing modules, wherein each experiment workflow comprises at least one workflow item, each comprising of at least one workflow step, wherein each workflow step is specified by a type and/or by a required resource and/or by a parameter set comprising at least one parameter describing the values to be set, wherein within at least one workflow step a user is free to move within an allowed variability, wherein the data processing system comprises an offline planning module, by which in an offline planning routine, the nominal experiment workflow is defined based on user input wherein the data processing system comprises a monitoring module, by which in a monitoring routine, monitoring information relating to real life workflow steps is retrieved from the laboratory and stored during the experiment, the monitoring information received from one or more sensors, wherein the data processing system comprises an execution module, by which in an execution routine, control information is provided to the user and/or the laboratory regarding the execution of oncoming nominal workflow steps, wherein the data processing system comprises a noncompliance module, by which in a noncompliance routine, based on the monitoring information, noncompliance of the real life experiment workflow by the user outside of the allowed variability with the nominal experiment workflow is detected based on noncompliance criteria and in case of detection of noncompliance. a reaction routine is activated by the noncompliance module, wherein in the reaction routine, a warning is presented to the user via the user interface, wherein the offline planning module configured such that in the offline planning routine, for at least one nominal workflow item an allowed variability, within which the at least one of the nominal workflow items is free to move, regarding at least one of the number, the type, the resource and the parameter set of the at least one nominal workflow step may be manually defined and that the noncompliance module is configured such that in the noncompliance routine, the criteria for noncompliance are fulfilled by, according to the monitoring information, a real life workflow item having moved beyond the allowed variability of the corresponding nominal workflow item of the nominal experiment workflow, and wherein when the real life workflow item has moved beyond the allowed variability the biological experiment terminates.

15. A computer readable storage media of claim 14 stored in a non-transitory manner, the computer readable storage media for a data processing system comprising:
   at least one sensor; and
   a plurality of data processing modules;
   wherein each experiment workflow comprises at least one workflow item, each comprising at least one workflow step, wherein each workflow step is specified by a type and/or by a required resource and/or by a parameter set comprising at least one parameter describing the values to be set,
   wherein within at least one workflow step a user is free to move within an allowed variability,
   wherein the data processing system comprises an offline planning module, by which in an offline planning routine, the nominal experiment workflow is defined based on user input wherein the data processing system comprises a monitoring module, by which in a monitoring routine, monitoring information relating to real life workflow steps is retrieved from the laboratory and stored during the experiment, the monitoring information received from one or more sensors,
   wherein the data processing system comprises an execution module, by which in an execution routine, control information is provided to the user and/or the laboratory regarding the execution of oncoming nominal workflow steps,
   wherein the data processing system comprises a noncompliance module, by which in a noncompliance routine, based on the monitoring information, noncompliance of the real life experiment workflow by the user outside of the allowed variability with the nominal experiment workflow is detected based on noncompliance criteria and in case of detection of noncompliance, a reaction routine is activated by the noncompliance module,
   wherein in the reaction routine, a warning is presented to the user via the user interface, wherein the offline planning module configured such that in the offline planning routine, for at least one nominal workflow item an allowed variability, within which the at least one of the nominal workflow items is free to move, regarding at least one of the number, the type, the resource and the parameter set of the at least one nominal workflow step may be manually defined and that the noncompliance module is configured such that in the noncompliance routine, the criteria for noncompliance are fulfilled by, according to the monitoring information, a real life workflow item having moved beyond the allowed variability of the corresponding nominal workflow item of the nominal experiment workflow, and
   wherein when the real life workflow item has moved beyond the allowed variability the biological experiment terminates.

16. The method according to claim 1, wherein in the offline planning routine, for each of the nominal workflow items an allowed variability regarding at least one of the number, the type, the resource and the parameter set of the at least one nominal workflow step is individually defined.

17. The method according to claim 6, wherein that with each execution of a real life workflow step, in the inline planning routine, the oncoming nominal workflow steps are adjusted.

18. The method according to claim 9, wherein that the optimization criteria are directed to the minimization of costs and/or time consumption.

19. The method of claim 1, wherein the resource comprises a pipette, mixer, or media.

* * * * *